United States Patent
Elliott

(10) Patent No.: US 7,713,212 B2
(45) Date of Patent: May 11, 2010

(54) METHOD AND SYSTEM FOR CONSCIOUSLY SYNCHRONIZING THE BREATHING CYCLE WITH THE NATURAL HEART RATE CYCLE

(75) Inventor: Stephen Bennett Elliott, Allen, TX (US)

(73) Assignee: Coherence LLC, Allen, TX (US)

(*) Notice: Subject to any disclaimer, the term of this patent is extended or adjusted under 35 U.S.C. 154(b) by 1020 days.

(21) Appl. No.: 10/699,025

(22) Filed: Nov. 3, 2003

(65) Prior Publication Data

US 2005/0096555 A1 May 5, 2005

(51) Int. Cl.
  *A61B 5/02* (2006.01)
(52) U.S. Cl. .................................... 600/500
(58) Field of Classification Search .......... 600/483, 600/484, 520, 509, 523
  See application file for complete search history.

(56) References Cited

U.S. PATENT DOCUMENTS

| | | | |
|---|---|---|---|
| 4,519,395 A | | 5/1985 | Hrushesky |
| 5,997,482 A | * | 12/1999 | Vaschillo et al. ............ 600/484 |
| 6,050,951 A | * | 4/2000 | Friedman et al. ............ 600/485 |
| 6,212,135 B1 | | 4/2001 | Schreiber |
| 6,301,499 B1 | | 10/2001 | Carlson et al. |
| 6,529,772 B2 | * | 3/2003 | Carlson et al. ............ 600/510 |
| 6,836,681 B2 | * | 12/2004 | Stabler et al. ............ 600/515 |
| 7,117,032 B2 | | 10/2006 | Childre et al. |
| 7,163,512 B1 | | 1/2007 | Childre et al. |
| 7,255,672 B2 | | 8/2007 | Elliott |
| 2005/0096555 A1 | | 5/2005 | Elliott |
| 2005/0209503 A1 | | 9/2005 | Elliott |
| 2005/0288601 A1 | | 12/2005 | Wood et al. |
| 2007/0056582 A1 | | 3/2007 | Wood et al. |
| 2007/0173684 A1 | | 7/2007 | Elliott |

OTHER PUBLICATIONS

StressEraser, http://www.stresseraser.com homepage, downloaded Oct. 11, 2007, 4 pages.

* cited by examiner

*Primary Examiner*—Mark W Bockelman
(74) *Attorney, Agent, or Firm*—Withrow & Terranova, PLLC

(57) ABSTRACT

The present invention provides a biofeedback system and method for the purpose of allowing a human subject to consciously synchronize one's rhythm of breathing with one's natural heart rhythm for purposes of maximizing coherence of one's heart rate variability pattern and consequent enhancement of physiological/psychological well being. It accomplishes this by facilitating a biofeedback signal that indicates to the human subject precisely when to inhale and exhale such that the breathing cycle will achieve a high degree of alignment with the natural heart rate cycle. It also specifies an instructive method for bringing a human subject to an adequately coherent heart rate variability pattern such that the preferred embodiment of the invention can be applied.

15 Claims, 6 Drawing Sheets

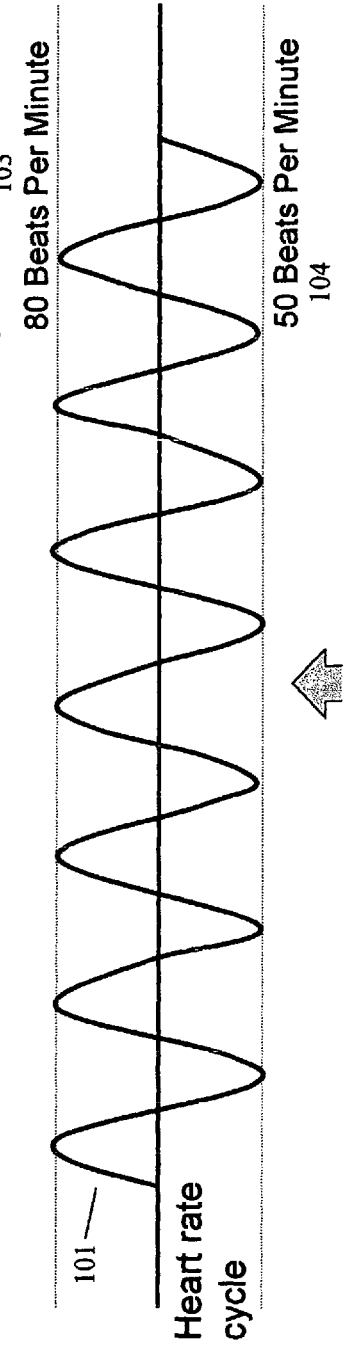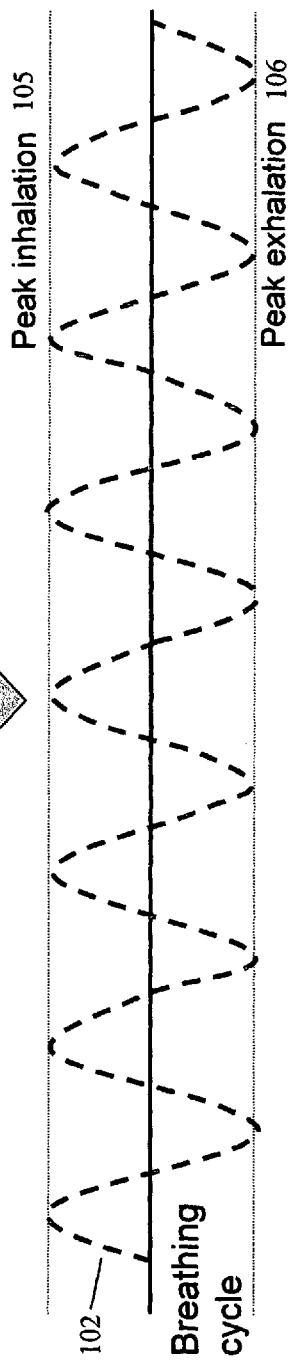

Figure 2

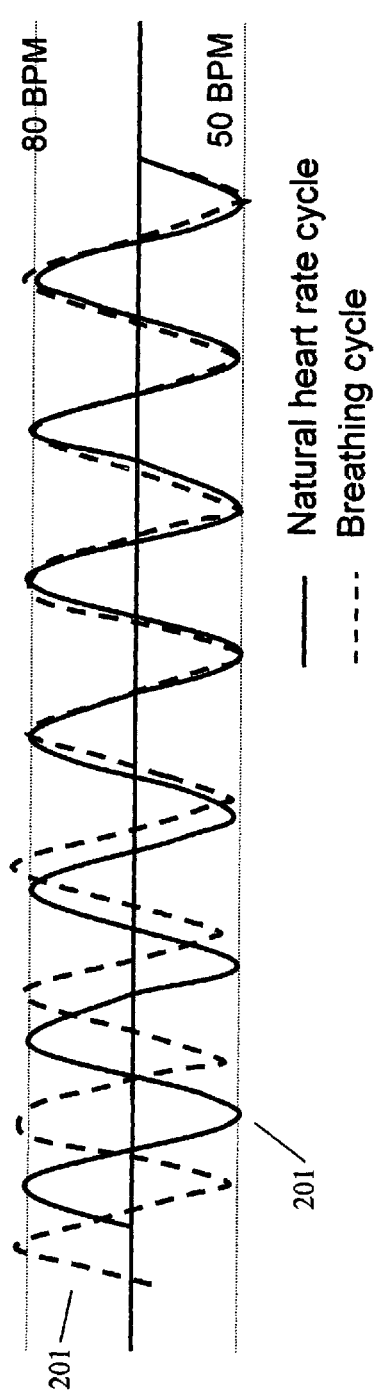
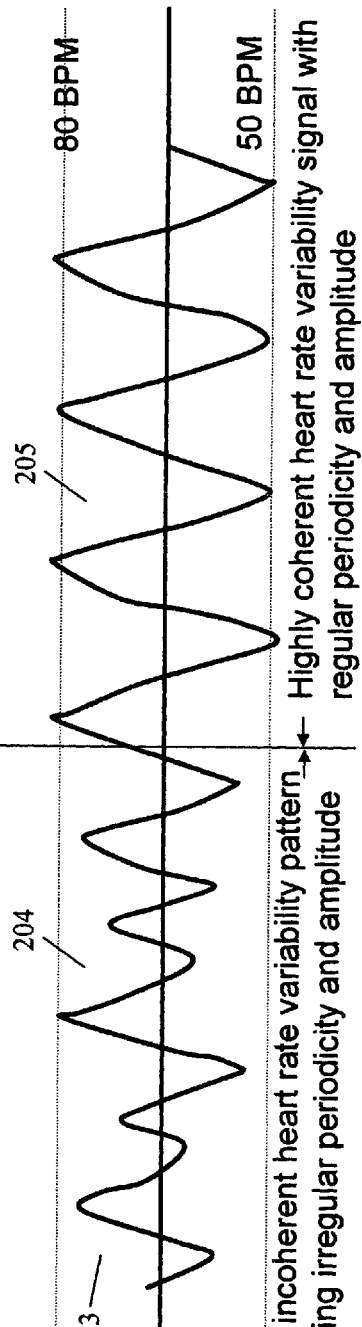

Depicts the breathing cycle and the natural heart rate cycles moving from misalignment to alignment.

— Natural heart rate cycle
--- Breathing cycle

Resultant heart rate variability pattern:

Highly incoherent heart rate variability pattern exhibiting irregular periodicity and amplitude Highly coherent heart rate variability signal with regular periodicity and amplitude Depicts heart rate signal and moment of biofeedback signal generation.

Physical system of preferred embodiment

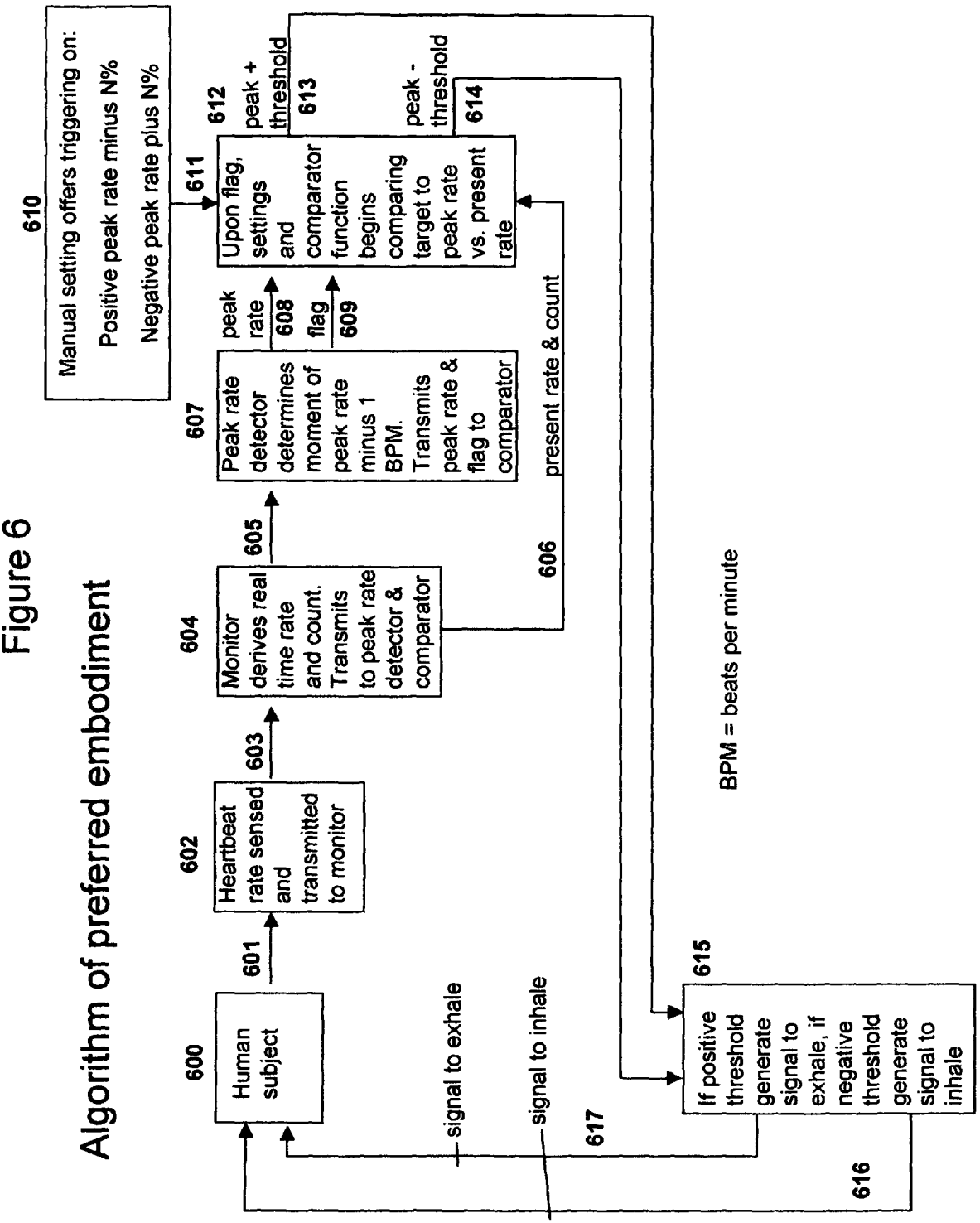

METHOD AND SYSTEM FOR CONSCIOUSLY SYNCHRONIZING THE BREATHING CYCLE WITH THE NATURAL HEART RATE CYCLE

FIELD OF THE INVENTION

The present invention relates to human physiology, and in particular to a method and system of biofeedback allowing a human subject to consciously control physiological processes, more particularly, it allows a human subject to achieve synchronization of one's breathing cycle with one's natural heart rate cycle.

BACKGROUND OF THE INVENTION

The human heart is known to have its own nervous system and its own natural tendency toward rhythm. For purposes of this invention, there are two primary aspects to this rhythm, the heartbeat rate, and the rate at which the heartbeat rate changes otherwise known as heart rate variability. Heartbeat rate is usually specified in absolute number of heartbeats occurring during a specified period. Heartbeat rate variability, otherwise know as heart rate variability is the change in heartbeat rate as occurs during a specified period. Henceforth, heartbeat rate variability will be referred to as heart rate variability.

While the heart has its own tendency toward rhythm, it is closely coupled to breathing. The relationship is such that as inhalation occurs, the heartbeat rate tends to increase and as exhalation occurs, the heartbeat rate tends to decrease. It is important to note that while the heartbeat rate and breathing rate influence each other, the relationship is an asynchronous one, that is, they are independent rhythms that influence but do not directly control each other.

It is generally recognized that heart rate variability is an indicator of physiological and emotional state, that is, irregular incoherent heart rate variability indicates a condition of physiological/psychological stress. Alternatively, highly coherent heart rate variability is indicative of a condition of physiological/psychological harmony.

Accordingly, it is highly desirable to achieve and maintain a highly coherent heart rate variability as life circumstances permit. This having been said, with proper training and the application of the method and apparatus of the present invention, it is possible for a human subject to rapidly achieve the desired state of high coherence of heart rate variability and to monitor and reinforce the accuracy and performance of said coherence on an ongoing basis.

The present invention takes advantage of the relationship between the breathing cycle and the natural heart rate variability cycle to bring heart rate variability to the desired state of coherence and the human subject to the resultant state of physiological and emotional harmony. It accomplishes this via conscious synchronization of the breathing cycle with the natural heart rate variability cycle.

SUMMARY OF THE INVENTION

As previously described, a relationship exists between the heartbeat rate specified in terms of heart rate variability, and the breathing cycle. While the heart has its own tendency toward a natural variable rhythm, there is a strong correlation with breathing according to this specific relationship: as inhalation occurs, there is a tendency for the heartbeat rate to increase, as exhalation occurs, there is a tendency for the heartbeat rate to decrease. It is important to note that the relationship between the natural heart rate variability cycle and the breathing cycle is indirect. This is to say that while the heart rate variability cycle/breathing cycle relationship exists, in untrained subjects, their alignment appears highly random. Consequently, these same subjects exhibit a highly incoherent heart rate variability pattern. As previously stated, maximal coherence of the heart rate variability is achieved when the cycle of breathing is synchronized with the natural heart variability cycle in time and amplitude. The most direct and effective manner of achieving this alignment is for the human subject to consciously align them via biofeedback, i.e., present the human subject with a biofeedback signal that indicates exactly when to inhale and exactly when to exhale such that the breathing cycle achieves exacting alignment with the natural heart rate variability cycle. The present invention achieves this by asserting a biofeedback signal to exhale just after the peak positive heartbeat rate has been reached and a biofeedback signal to inhale just after the peak negative heartbeat rate has been reached. Closely aligning the natural heart rate peaks with breathing peaks is critical to achieving an overall synchronization and resulting high degree of coherence of the heart rate variability pattern.

For purposes of the present invention, we can consider the cycles of heart rate variability, the periodicity of increasing and decreasing of heartbeat rate, and the breathing cycle, the periodicity of inhalation and exhalation, to be two independent cycles as depicted in FIG. 1. The relative synchronization of these cycles can vary between 0 and 180 degrees. When these cycles are completely out of phase, heart rate variability is maximally incoherent, when these cycles are completely in phase heart rate variability is maximally coherent.

The invention defines the system and method of the application of biofeedback for purposes of providing a human subject the ability to consciously control their inhalation and exhalation so as to achieve the desired coherence of heart rate variability. A present objective is to achieve maximal alignment. As this is an emerging field of inquiry, it is entirely likely that applications of value will be found for other alignments, for example maximal misalignment, 45 degree out of phase, etc. It is understood that these alternative alignments are also within the scope of the present invention.

Because the heart rate variability signal of the untrained subject is typically highly erratic and synchrony of said signal may be difficult to detect, a specific instructive method employing other biofeedback devices and methods is specified. Via the application of this instructive method, the human subject is led to achieve a detectable level of synchrony of their heart rate variability signal. Once detected, the present invention can be readily used to achieve optimal alignment of the subject's breathing cycle with their natural heart rate variability cycle.

BRIEF DESCRIPTION OF THE DRAWING FIGURES

The accompanying drawing figures incorporated in and forming a part of this specification illustrate several aspects of the invention, and together with the description serve to explain the principles of the invention.

FIG. 1 depicts the relative relationship between the natural heart rate cycle and breathing cycle.

FIG. 2 depicts the natural heart rate cycle and breathing cycle moving from misalignment to alignment and resultant heart rate variability pattern.

FIG. 6 depicts the algorithm for the preferred embodiment of the present invention.

DETAILED DESCRIPTION OF THE PREFERRED EMBODIMENTS

Figure 3:
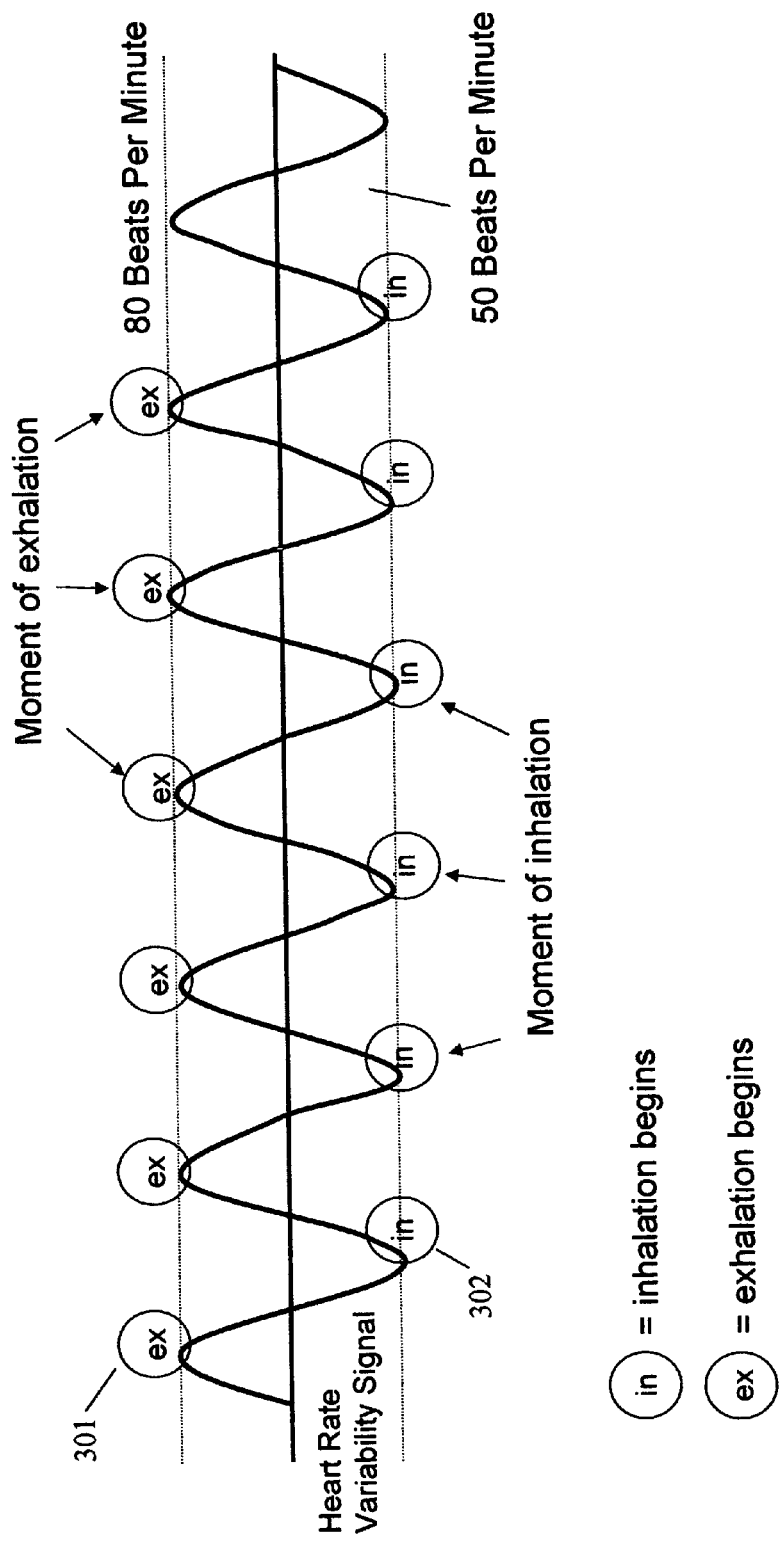
FIG. 3 depicts a primary example of the moment of biofeedback signal generation according to a preferred embodiment of the present invention.

The embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

The present invention allows a human subject to achieve maximal regularity and coherence of heart rate variability by synchronizing the breathing cycle with the natural heart rate variability cycle. This is accomplished by providing a biofeedback signal in the form of an audible, visual, or sensory stimulus, to indicate when the subject should begin inhalation and a second signal to indicate when the subject should begin exhalation. These signals are unique so the subject is able to clearly distinguish the beginning of inhalation from the beginning of exhalation.

With reference to FIG. 1, the heart has its own nervous system and a tendency toward its own natural rhythm. FIG. 1 depicts the heart rate variability cycle, 101, and the breathing cycle, 102. The positive peak of the heart rate variability cycle, 103, indicates peak positive heart rate or the maximum number of heart beats per minute. For the purposes of discussion the peak positive rhythm is defined as 80 beat per minute (BPM). The negative peak of the heart rate variability cycle, 104, indicates peak negative heart rate or the minimum number of heart beats per minute. For the purposes of discussion the peak positive rhythm is defined as 50 beat per minute (BPM). Let it be clear that 80 beats per minute as the positive peak and 50 beats per minute as the negative peak are merely used for purposes of example. The breath is under control of the human central nervous system and operates with a largely independent rhythm. Yet, there is a strong correlation between the breath cycle and the natural heart rate variability cycle as described prior.

FIG. 2 depicts the breathing cycle 201 and the natural heart rate cycle 202 moving from misalignment to alignment and the resultant heart rate variability cycle 203 moving from incoherence 204 to coherence 205. The synchrony between the natural heart rate variability cycle and the cycle of breathing is highly variable ranging from being highly synchronous (in-phase) to being highly asynchronous (out of phase). This results in a highly periodic and coherent heart rate variability pattern 205 vs. a highly aperiodic and incoherent heart rate variability pattern 204, respectively. A primary yet not limiting application of the present invention is to lead a human subject to the preferred state of highly periodic and coherent heart rate variability both in time and amplitude.

FIG. 3, depicts the natural heart rate cycle and the moments of biofeedback signal generation indicating exhalation 301 and inhalation 302. The desired state of highly periodic and coherent heart rate variability is brought about by aligning the cycle of breathing with the natural heart rate cycle. This is accomplished by monitoring the heart rate signal and providing biofeedback to the human subject so as to allow the subject to synchronize their inhalation and exhalation so as to be in phase with their heart rate pattern. This requires that the human subject begin inhaling as the natural heart rate signal begins increasing from its negative peak, and conversely, to begin exhaling as the natural heart rate begins decreasing from its positive peak.

It should be noted that for purposes of biofeedback generation, the exact moment of alerting occurs slightly after the positive and negative peaks are reached. This will be explained in greater detail below.

It must be further explained that while FIG. 3 depicts the primary application of the present invention, that being the maximal alignment of the heart rate variability cycle and the breathing cycle, all other alignments are also provided for and are within the scope of the present invention.

Figure 4:
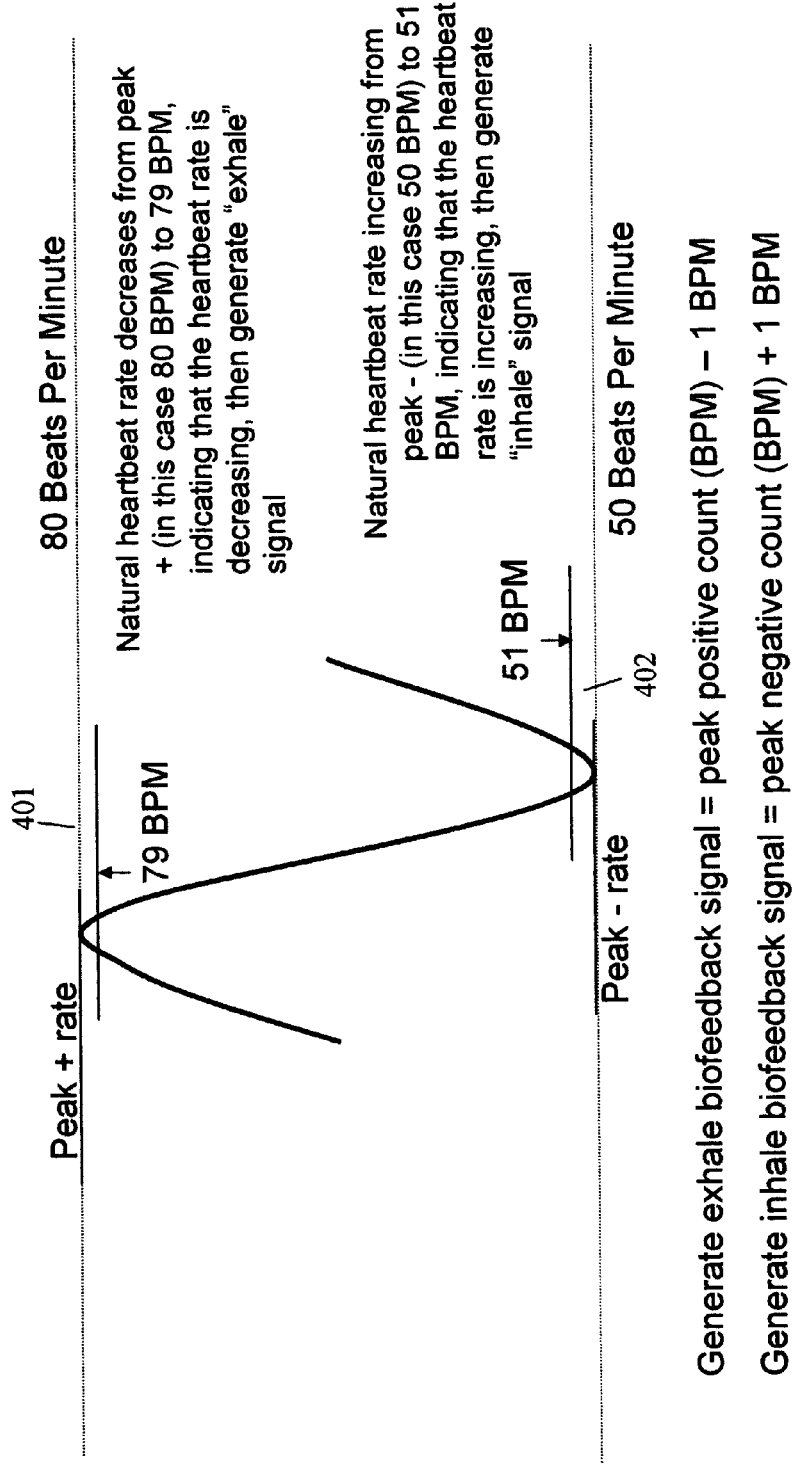
FIG. 4 depicts specific criterion for biofeedback signal generation associated with the primary example of the moment of biofeedback signal generation of FIG. 3.
Figure 5:
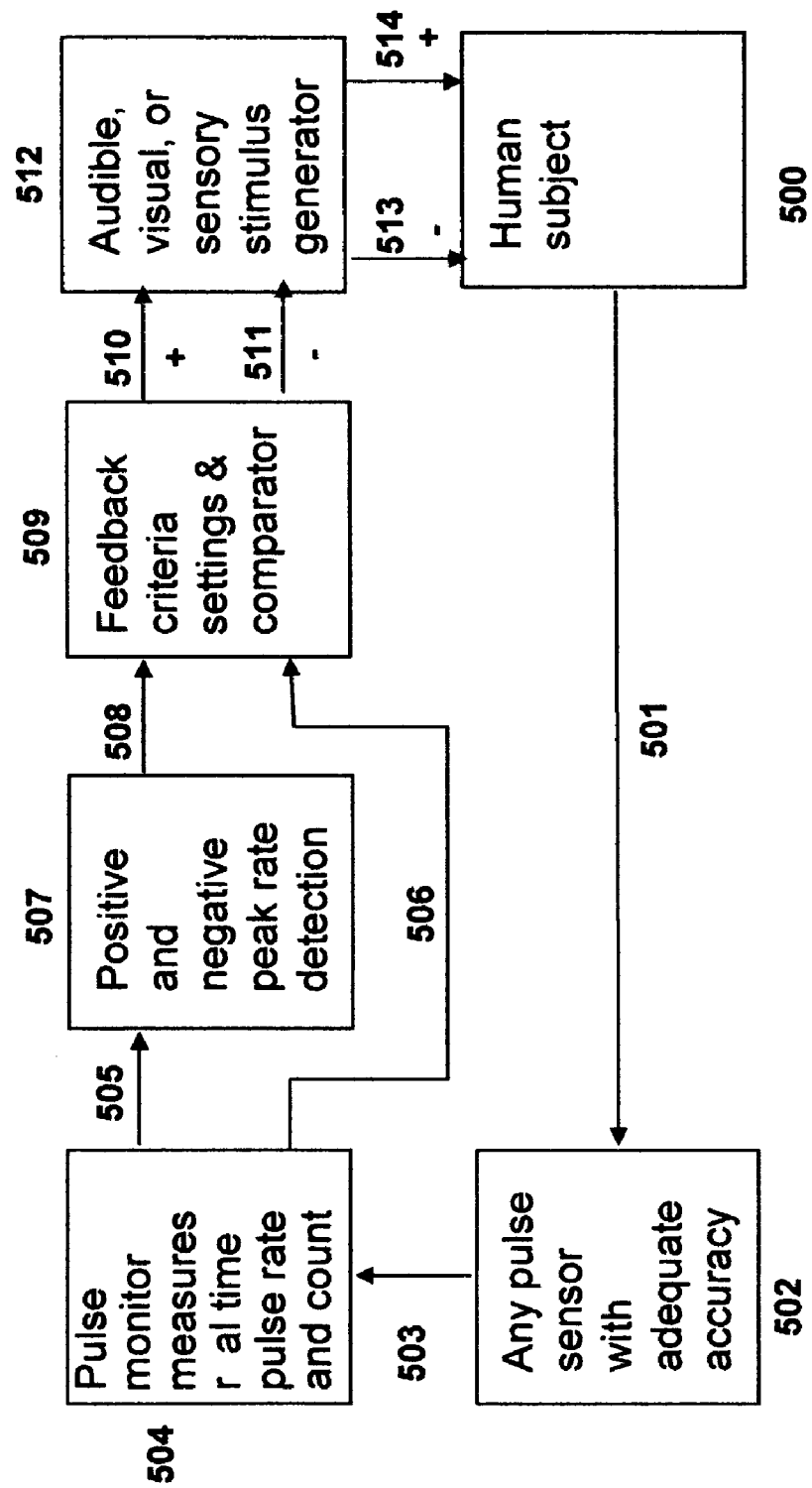
FIG. 5 depicts the physical system of the preferred embodiment of the present invention.

FIG. 4 depicts the exacting means of identifying positive and negative heart rate peaks. With reference to FIG. 4, in order to achieve maximal desired effect, it is necessary to achieve a very exacting timing. Here it is important to point out that via biofeedback, the human subject is trained to identify the subjective state and associated sensation that relates to maximal alignment. If the human subject begins either inhaling or exhaling just slightly before the natural heart rate begins to increase or decrease respectively, the periodicity and coherence of the resulting heart rate variability pattern is significantly degraded. This suboptimal coherence of heart rate variability can be consciously perceived by the practitioner. To address this matter of accuracy, in this example, the "exhale" biofeedback signal is generated just after the positive peak, in this case 80 beats per minute (BPM), when the signal drops to 79 beats per minute (BPM) 401. Likewise, the "inhale" biofeedback signal is generated just after the negative peak, in this case 50 beats per minute (BPM), when the signal increases to 51 beats per minute (BPM) 402. Because, in order to achieve the desired maximal effect this timing must be exacting, the present invention allows for the exact moment of biofeedback to be adjusted so that timing may be optimized on a personal basis. This would allow for slightly differing physiologies if such differences are found to exist. Programmability of biofeedback signal generation is also provided to accommodate other useful alignments of the natural heart rate cycle and breathing cycle should such useful alignments be found to exist. With reference to FIG. 5, the primary physical system of the preferred embodiment of the present invention is quite simple consisting of a human subject 500, a pulse sensor of adequate accuracy 502, a pulse monitor of adequate accuracy 504, a positive and negative peak rate detector 507, a function for setting feedback criterion and comparing it 509, and a function for generating feedback signals to the human subject 512.

A detailed discussion of the physical system will now ensue. Human subject 500 is outfitted with a pulse sensor 502 of any adequately accurate variety, via connection 501. Sensor 502 and associated connection 501 may be of any adequately accurate type including electronic, pneumatic, acoustic, etc. The sensor may be any style of device such as a wristband, a finger cradle, an ear clip, etc. The only requirement is that it be able to accurately sense and transmit individual heart beat pulses to pulse monitor 504 via connection 503. Connection 503 may also be of any adequately performing type including electronic, pneumatic, acoustic, optical, radio frequency, etc. Pulse monitor 504 monitors real time rate and count. Heartbeat count is used as an alternative means of feedback for purposes of allowing the human subject to synchronize their breathing based on heartbeat count as opposed to a predetermined threshold. For example, instead of using the inhale/exhale signal as the basis of controlling the breathing cycle, a human subject may desire to count 1-2-3-4-5-6-begin exhaling-1-2-3-4-5-begin inhaling, etc. Pulse monitor 504 sends this information to positive and negative peak rate detector 507 via connector 505 and to feedback and criteria settings and comparator 509. Positive and negative peak rate detector 507 detects when peak pulse rate occurs, and signals to feedback criteria settings and comparator 509 via connector 508 that, a) peak pulse rate has occurred and b) the value of the peak pulse rate. Based on the receipt of the peak pulse rate signal via connector 508, criteria settings and comparator 509, begins comparing peak pulse rate vs. present pulse rate against previously established settings to determine the moment when the biofeedback signal associated with the positive peak or negative peak should be asserted to audible, visual, or sensory stimulus function 512, via connectors 510 and 511, 510 relating to positive peak and 511 relating to negative peak. Upon receipt of positive peak signal via connector 510, audible, visual, or sensory stimulus generator 512, generates a biofeedback signal to human subject 500 via positive peak connector 514 indicating exhale. Likewise, upon receipt of negative peak signal via connector 511, audible, visual, or sensory stimulus generator 512, generates a biofeedback signal to human subject 500 via negative peak connector 513 indicating "inhale". This system applies to any adequately accurrate analog or digital method of sensing, measuring, decision making, and feedback generation. Programmability of biofeedback signal generation occurs on the basis of peak positive and peak negative heart beat rates and on the basis of peak positive and peak negative heart beat rates plus respective offsets. Programmable offsets are provided on the basis of the present heart beat rate as a percentage of the peak heart beat rate, on the basis of the present heart beat rate vs. peak heart beat rate, on the basis of the absolute number of heart beats since peak heart beat rate, and on the basis of individual heart beats. Unique programmability applies to positive negative peaks, that is, to exhalation and inhalation phases, respectively.

With reference to FIG. 6, for clarity, the algorithm of the preferred embodiment of the present invention shall now be discussed. The heartbeat rate of a human subject 600 is sensed via sensor 602 via connector 601. Sensor 602 detects the heartbeat rate and transmits its analog or digital equivalent with adequate accuracy to monitor 604 via connector 603. Monitor 604 derives the real time heartbeat rate, heartbeat count, and transmits its analog or digital equivalent to peak rate detector 607 and settings and comparator function 611 via connectors 605 and 606 respectively. Peak rate detector 607 determines the exact moment of peak rate by analyzing the present rate for maximum positive rate minus 1 heart beat per minute (BPM) and maximum negative rate plus 1 heart beat per minute (BPM) for positive and negative peaks respectively. At the moment of detection, peak rate detector 607 sends the rate 608 and a flag 609 to the settings and comparator function 612. Upon receipt of the flag 609, the settings and comparator function 612 begins comparing manual settings 610 via 611 with the peak rate 608 vs. present rate 606. When the threshold is achieved, settings and comparator function 612 sends a positive peak threshold signal 613 or a negative peak threshold signal 614 to audible, visual, or sensory stimulus generator 615. This threshold is totally programmable and may be programmed in: a) number of heartbeats or, b) percent of peak rate. Upon receipt, audible, visual, or sensor stimulus generator 615 generates a signal to exhale 617 or signal to inhale 616 respectively. This programmability is provided for both positive and negative peaks.

This is to say, that offsets associated with the positive peak and with beginning exhalation and offsets associated with the negative peak and with the beginning of inhalation are individually programmable. For example, the offset associated with the positive peak may be "zero" and the offset associated with the negative peak may be 10%.

Instructive Method:

Typically, the heart rate variability pattern of the untrained subject is highly irregular and may resemble random noise. For this reason, it may be difficult to detect the moments of peak positive and peak negative heart rate with a regularity that can be discerned and employed by the human subject. Therefore, the present instructive method is specified to bring a human subject to an initial physiological/psychological state such that the present invention may be employed effectively.

The heart rate variability signal is generally considered to represent the relative balance of sympathetic and parasympathetic nervous systems. For this reason, the heart rate variability pattern is highly indicative of the psycho-physiological state of the human subject with this general relationship: anxiety and tension result in incoherence of the heart rate variability pattern, harmony and calm result in coherence of the heart rate variability pattern. It is often necessary for an untrained human subject to reduce their level of anxiety and tension before an adequately coherent heart rate variability pattern can be detected and used effectively for specifying when to inhale and when to exhale. This tension and anxiety is most easily assessed and reduced via application of electromyographic (EMG) and electroencephalographic (EEG) biofeedback methods and apparatus as tension and anxiety follow this general relationship with EMG and EEG:

EMG: as tension and anxiety increase, muscle activation increases with a resultant increase in measured voltage.

EEG: as tension and anxiety increase, brainwaves in the high beta bands (frequencies between 19 Hertz and 33 Hertz) increase in amplitude.

Therefore, to bring the human subject to an adequate state of coherence of the heart rate variability pattern, the following steps are specified:

Step 1: The human subject is asked to position themselves comfortably in a chair in an upright posture. The apparatus of the present invention is connected to the subject and the coherence of the heart rate variability signal or lack thereof is established. If the signal is not adequately coherent to effectively detect positive and negative heart rate peaks, an electromyographic measurement device is placed on the skin just over the major muscle of the jaw on either side of the face in the general vicinity of the superficial portion of the masseter muscle. The electrical signal resulting from this tension is presented to the subject using electromyographic apparatus. The subject is requested to consciously relax this area as deeply as possible. After the subject has demonstrated the ability to reduce the tension in this area to an acceptable level, the present invention is once again applied and coherence of the heart rate variability is once again assessed. If adequate coherence is detected, the human subject is asked to spend some time consciously examining the relationship between tension in the area of the masseter muscle and the coherence of their heart rate variability signal as indicated by the regularity of biofeedback indications to inhale and exhale. If adequate coherence is detected, the subject is asked to begin following biofeedback cues to inhale and exhale accordingly.

Step 2: If an acceptable EMG signal is achieved during the prior step but an adequately coherent heart rate variability is still not detected, an electroencephalograph is employed using conventional electrode placement. The subject's high beta brainwave bands are monitored, and feedback is provided. The subject is first asked to consciously lower the amplitude of high beta frequencies centered around 26 Hertz. This process is aided via helpful suggestions by the practitioner. When the subject has achieved an adequately low amplitude in this frequency band, the apparatus of the present invention is applied and the coherence of the heart rate variability signal is assessed. If adequate coherence is detected, the subject is requested to examine the relationship between their beta amplitude and their heart rate variability signal. If adequate coherence is detected, the subject is requested to begin following biofeedback cues to inhale and exhale accordingly.

Step 3: If an acceptable EEG in the 26 Hertz band is achieved but an adequately coherent heart rate variability is still not detected, the same process is repeated for the next lower beta band centered around 20 Hertz.

Step 4: By the end of this process, the subject will most likely achieve adequate coherence of heart rate variability as detected by the apparatus of the present invention. Once this is achieved, the subject is requested to begin following biofeedback cues to inhale and exhale accordingly.

Once the human subject has become proficient in establishing and maintaining the desired coherence of heart rate variability, in principle, the apparatus may be utilized whenever and wherever the subject desires. It is assumed that the apparatus is fully capable and of a size making it fully portable.

Given that this is an emerging field of investigation, it is highly likely that it will be found that other physiological and psychological functions can be enhanced by synchronizing them with this fundamental bio-resonance. For example, synchronization of running, walking, cycling, talking, exercising, thinking, meditating, etc. Those skilled in the art will recognize improvements and modifications to the preferred embodiments of the present invention. All such improvements and modifications are considered within the scope of the concepts disclosed herein and the claims that follow.

What is claimed is:

1. A method for consciously synchronizing a breathing cycle of a human subject with a natural heart rate of the human subject, the method comprising: monitoring the natural heart rate of the human subject; detecting a transition in the natural heart rate from a maximum heart rate;
    providing a first biofeedback signal to the human subject to indicate that the natural heart rate has reached the maximum heart rate;
    detecting a transition in the natural heart rate from a minimum heart rate;
    providing a second biofeedback signal to the human subject to indicate that the natural heart rate has reached the minimum heart rate; and
    instructing the human subject as to the exact moment to begin inhalation by instructing the patient to begin inhalation upon receiving the second feedback signal and instructing the human subject as to the exact moment to begin exhalation by instructing the patient to exhale upon receiving the first feedback signal, such that the human subject aligns their breathing with the natural heart rate to attempt to achieve consistency in the natural heart rate, wherein the instruction provided to the human subject to begin exhalation is provided by a first feedback type and the instruction provided to the human subject to begin inhalation is provided by a second feedback type.

2. The method of claim 1 further comprising synchronizing the exact moment to begin inhalation with increasing heart rate associated with the detection of the transition in the natural heart rate from the minimum heart rate and synchronizing the exact moment to begin exhalation with decreasing heart rate associated with the detection of the transition in the natural heart rate from the maximum heart rate.

3. The method of claim 1 wherein instructing the exact moment to begin inhalation comprises providing the second feedback type on the basis of peak negative heart rate and wherein instructing the exact moment to begin exhalation comprises providing the first feedback type on the basis of peak positive heart rate.

4. The method of claim 1 further comprising instructing the human subject on the exact moment to begin inhalation on the basis of peak negative heart rate plus one (1) heart beat and instructing the human subject on the exact moment to begin exhalation on the basis of peak positive heart rate minus one (1) heart beat.

5. The method of claim 1, wherein:
    providing the first biofeedback signal includes providing the first biofeedback signal at the maximum heart rate minus a first programmable offset; and
    providing the second biofeedback signal includes providing the second biofeedback signal at the minimum heart rate plus a second programmable offset.

6. The method of claim 5 wherein the first biofeedback signal informs the human subject to begin to exhale.

7. The method of claim 5 wherein the second biofeedback signal informs the human subject to begin to inhale.

8. The method of claim 5 wherein the first programmable offset is a percentage of the maximum heart rate of the human subject.

9. The method of claim 5 wherein the second programmable offset is a percentage of the minimum heart rate of the human subject.

10. The method of claim 5 wherein the first programmable offset is a number of heart beats after the maximum heart rate of the human subject.

11. The method of claim 5 wherein the second programmable offset is a number of heart beats after the minimum heart rate of the human subject.

12. The method of claim 5 further comprising presenting the human subject with a number of heart beats since the minimum heart rate and a number of heart beats since the maximum heart rate such that the human subject can consciously synchronize their own inhalation and exhalation on the basis thereof, respectively.

13. The method of claim 1 further comprising providing individual heart beats to the human subject in at least one of an audible, visual, and sensory format.

14. The method of claim 1 further comprising providing the first and second biofeedback signals on the basis of at least one of peak positive heart rate and peak negative heart rate.

15. The method of claim 1 further comprising instructing the human subject to synchronize a peak of an exhalation phase of a breathing cycle for the human subject with a peak negative heart rate and to synchronize a peak of an inhalation phase of the breathing cycle with a peak positive heart rate.

* * * * *